(12) United States Patent
Mori

(10) Patent No.: US 10,401,338 B2
(45) Date of Patent: Sep. 3, 2019

(54) PLASMA PROCESSING DETECTION INDICATOR

(71) Applicant: SAKURA COLOR PRODUCTS CORPORATION, Osaka-shi, Osaka (JP)

(72) Inventor: Marimo Mori, Osaka (JP)

(73) Assignee: SAKURA COLOR PRODUCTS CORPORATION, Osaka-shi (JP)

(*) Notice: Subject to any disclaimer, the term of this patent is extended or adjusted under 35 U.S.C. 154(b) by 114 days.

(21) Appl. No.: 15/117,601

(22) PCT Filed: Feb. 12, 2015

(86) PCT No.: PCT/JP2015/053742
§ 371 (c)(1),
(2) Date: Aug. 9, 2016

(87) PCT Pub. No.: WO2015/122425
PCT Pub. Date: Aug. 20, 2015

(65) Prior Publication Data
US 2016/0349222 A1 Dec. 1, 2016

(30) Foreign Application Priority Data

Feb. 14, 2014 (JP) .................... 2014-026849

(51) Int. Cl.
| | | |
|---|---|---|
| G01D 7/00 | (2006.01) | |
| G01N 31/22 | (2006.01) | |
| H01J 37/32 | (2006.01) | |

(52) U.S. Cl.
CPC ............ *G01N 31/22* (2013.01); *G01D 7/005* (2013.01); *H01J 37/32009* (2013.01);
(Continued)

(58) Field of Classification Search
CPC ... G01N 31/22; G01D 7/005; H01J 37/32009; H01J 37/3244; H01J 2237/334; H01J 37/32917; H01J 37/32935; H01J 37/32972
(Continued)

(56) References Cited

U.S. PATENT DOCUMENTS 3,568,627 A * 3/1971 Selinger .................. G01K 3/04
116/207
4,155,895 A    5/1979 Rohowetz et al.
(Continued)

FOREIGN PATENT DOCUMENTS

| CN | 1777644 A | 5/2006 |
|---|---|---|
| CN | 1877777 A | 12/2006 |

(Continued)

OTHER PUBLICATIONS

International Search Report dated Apr. 14, 2015, issued in counterpart International Application No. PCT/JP2015/053742 (1 page).
(Continued)

*Primary Examiner* — Justin Seo
*Assistant Examiner* — Tania C Courson
(74) *Attorney, Agent, or Firm* — Westerman, Hattori, Daniels & Adrian, LLP

(57) ABSTRACT

This invention provides a plasma treatment detection indicator that uses a fibrous base material or a synthetic resin base material comprising a coloring pigment as a base material and in which fine fiber pieces or coloring pigment is prevented from being generated in a powder form from the base material in plasma treatment. More specifically, this invention provides a plasma treatment detection indicator comprising a base material and at least a color-changing layer that changes color in a plasma treatment atmosphere, the color-changing layer being disposed above part or all of
(Continued)

a surface of the base material, (1) the base material being a fibrous base material or a synthetic resin base material comprising a coloring pigment, and (2) a resin-based or inorganic transparent cover layer that covers all of the surface of the base material being disposed between the base material and the color-changing layer.

5 Claims, 1 Drawing Sheet

(52) U.S. Cl.
CPC .... *H01J 37/3244* (2013.01); *H01J 37/32917* (2013.01); *H01J 37/32935* (2013.01); *H01J 37/32972* (2013.01); *H01J 2237/334* (2013.01)

(58) Field of Classification Search
USPC .................................. 116/206–207, 216–220
See application file for complete search history.

(56) References Cited

U.S. PATENT DOCUMENTS

| | | | |
|---|---|---|---|
| 4,179,397 A | 12/1979 | Rohowetz et al. | |
| 4,448,548 A * | 5/1984 | Foley | G01N 31/226 |
| | | | 252/408.1 |
| 4,839,311 A | 6/1989 | Riley et al. | |
| 5,955,025 A | 9/1999 | Barrett | |
| 5,990,199 A | 11/1999 | Bealing et al. | |
| 6,063,631 A | 5/2000 | Ignacio | |
| 6,117,685 A | 9/2000 | Omatsu et al. | |
| 6,238,623 B1 * | 5/2001 | Amhof | A61L 2/14 |
| | | | 116/206 |
| 6,267,242 B1 * | 7/2001 | Nagata | A61L 2/28 |
| | | | 206/459.1 |
| 6,355,448 B1 | 3/2002 | Foltz et al. | |
| 6,410,338 B1 * | 6/2002 | Lippold | A61L 2/28 |
| | | | 422/29 |
| 6,524,763 B1 | 2/2003 | Kuroda et al. | |
| 6,659,036 B2 * | 12/2003 | Omatsu | A61L 2/28 |
| | | | 116/206 |
| 6,852,281 B2 | 2/2005 | Inoue et al. | |
| 7,189,355 B2 | 3/2007 | Mikumo et al. | |
| 7,213,534 B2 * | 5/2007 | Siikaluoma | G01M 3/042 |
| | | | 116/200 |
| 7,364,700 B2 | 4/2008 | Maruo et al. | |
| 7,364,770 B2 | 4/2008 | Nagashima et al. | |
| 7,678,858 B2 | 3/2010 | Tanaka et al. | |
| 7,976,781 B2 | 7/2011 | Maruo et al. | |
| 7,981,687 B2 | 7/2011 | Yamaguchi et al. | |
| 8,343,437 B2 * | 1/2013 | Patel | G01K 3/04 |
| | | | 252/408.1 |
| 8,530,242 B2 | 9/2013 | Lin et al. | |
| 8,567,338 B2 * | 10/2013 | Greene | A61L 2/28 |
| | | | 116/206 |
| 9,168,086 B2 * | 10/2015 | Allen | A61B 18/14 |
| 9,194,808 B2 * | 11/2015 | Yamaguchi | A61L 2/14 |
| 9,944,061 B2 * | 4/2018 | Garhart | B32B 37/14 |
| 2001/0054374 A1 | 12/2001 | Omatsu et al. | |
| 2002/0051733 A1 | 5/2002 | Antonoplos et al. | |
| 2002/0121629 A1 | 9/2002 | Mikumo et al. | |
| 2005/0054374 A1 | 3/2005 | Namiki | |
| 2006/0194056 A1 | 8/2006 | Nagashima et al. | |
| 2006/0235140 A1 | 10/2006 | Tanaka et al. | |
| 2006/0244379 A1 | 11/2006 | Shin | |
| 2006/0283746 A1 | 12/2006 | Sutoh et al. | |
| 2008/0090726 A1 | 4/2008 | Eskra et al. | |
| 2008/0157486 A1 | 7/2008 | Kuzawa et al. | |
| 2008/0267811 A1 * | 10/2008 | Yamaguchi | G01N 31/223 |
| | | | 422/3 |
| 2009/0212237 A1 | 8/2009 | Sugiki et al. | |
| 2010/0119410 A1 | 5/2010 | Yamaguchi et al. | |
| 2011/0009535 A1 | 1/2011 | Mikumo et al. | |
| 2011/0065203 A1 | 3/2011 | Studer et al. | |
| 2011/0275159 A1 | 11/2011 | Landgrebe et al. | |
| 2011/0312096 A1 | 12/2011 | Whitman et al. | |
| 2012/0100395 A1 | 4/2012 | Feiler et al. | |
| 2012/0149037 A1 * | 6/2012 | Bommarito | C12Q 1/04 |
| | | | 435/7.33 |
| 2012/0315659 A1 | 12/2012 | Andreescu et al. | |
| 2014/0154808 A1 | 6/2014 | Patel | |
| 2014/0216636 A1 | 8/2014 | Kuzawa et al. | |
| 2015/0050745 A1 | 2/2015 | Karato et al. | |
| 2016/0045631 A1 | 2/2016 | Yamaguchi et al. | |
| 2016/0133444 A1 | 5/2016 | Oshiro et al. | |
| 2016/0141192 A1 | 5/2016 | Uneyama et al. | |
| 2016/0349222 A1 | 12/2016 | Mori | |
| 2016/0349224 A1 * | 12/2016 | Patel | G01K 3/04 |
| 2017/0044389 A1 | 2/2017 | Mori | |
| 2017/0101548 A1 | 4/2017 | Mori et al. | |
| 2017/0153174 A1 | 6/2017 | Yamakawa et al. | |
| 2017/0261476 A1 | 9/2017 | Hishikawa et al. | |
| 2017/0330777 A1 | 11/2017 | Hishikawa et al. | |

FOREIGN PATENT DOCUMENTS

| | | |
|---|---|---|
| CN | 101014668 A | 8/2007 |
| CN | 101230247 A | 7/2008 |
| EP | 1312918 A2 | 5/2003 |
| GB | 2 168 082 A | 6/1986 |
| JP | 54-088068 A | 7/1979 |
| JP | 63-36786 A | 2/1988 |
| JP | S63-36876 A | 2/1988 |
| JP | 1-295423 A | 11/1989 |
| JP | 4-305492 A | 10/1992 |
| JP | 6-69165 A | 3/1994 |
| JP | 7-26477 A | 1/1995 |
| JP | 11-37988 A | 2/1999 |
| JP | 2000-269191 A | 9/2000 |
| JP | 2001-174449 A | 6/2001 |
| JP | 2001-237097 A | 8/2001 |
| JP | 2001-242249 A | 9/2001 |
| JP | 2002-011081 A | 1/2002 |
| JP | 2002-022534 | 1/2002 |
| JP | 2002-502953 A | 1/2002 |
| JP | 2002-303618 A | 10/2002 |
| JP | 2002/322315 A | 11/2002 |
| JP | 2002-323451 A | 11/2002 |
| JP | 2003-506156 A | 2/2003 |
| JP | 2003-119087 | 4/2003 |
| JP | 2003-515744 A | 5/2003 |
| JP | 2003-325646 A | 11/2003 |
| JP | 2004-101488 A | 4/2004 |
| JP | 2004-146738 A | 5/2004 |
| JP | 2004-146739 A | 5/2004 |
| JP | 2004-203984 A | 7/2004 |
| JP | 2004-298479 A | 10/2004 |
| JP | 2005-111154 A | 4/2005 |
| JP | 2005-142287 A | 6/2005 |
| JP | 2005-315828 A | 11/2005 |
| JP | 2005-329019 A | 12/2005 |
| JP | 2006-78463 A | 3/2006 |
| JP | 2006-223351 A | 8/2006 |
| JP | 2007-40785 A | 2/2007 |
| JP | 2008-125760 A | 6/2008 |
| JP | 2009-213609 A | 9/2009 |
| JP | 2010-501655 A | 1/2010 |
| JP | 2011-530085 A | 12/2011 |
| JP | 2012-050664 A | 3/2012 |
| JP | 2012-068811 A | 4/2012 |
| JP | 2012-78202 A | 4/2012 |
| JP | 2013-95764 A | 5/2013 |
| JP | 2013-95765 A | 5/2013 |
| JP | 2013-98196 A | 5/2013 |
| JP | 2013-233387 A | 11/2013 |
| JP | 2014-109523 A | 6/2014 |
| JP | 2016-111063 A | 6/2016 |
| WO | 98/46279 A1 | 10/1998 |
| WO | 98/46994 A1 | 10/1998 |
| WO | 99/39754 A1 | 8/1999 |
| WO | 01/10476 A1 | 2/2001 |
| WO | 01/40792 A1 | 6/2001 |
| WO | 2004-087222 A1 | 10/2004 |

(56) References Cited

FOREIGN PATENT DOCUMENTS

| WO | 2006/109726 A1 | 10/2006 |
|---|---|---|
| WO | 2008/022952 A1 | 2/2008 |
| WO | 2009/128988 A1 | 10/2009 |
| WO | 2013/129473 A1 | 9/2013 |
| WO | 2014/038612 A1 | 3/2014 |
| WO | 2014/196440 A1 | 12/2014 |
| WO | 2015/025699 A1 | 2/2015 |
| WO | 2015/170592 A1 | 11/2015 |

OTHER PUBLICATIONS

Nagatsu, "3. Plasma Sterilization", J. Plasma Fusion Res., vol. 83, No. 7, pp. 601-606, The Japan Society of Plasma Science and Nuclear Fusion Research, 2007, Partial Translation. (7 pages).
Notice of Allowance dated Nov. 22, 2017, issued in U.S. Appl. No. 15/316,980 (15 pages).
Final Office Action dated Nov. 17, 2017, issued in U.S. Appl. No. 14/895,835 (18 pages).
International Search Report dated Sep. 2, 2014, issued in Application No. PCT/JP2014/064209 (4 pages).
English translation of Written Opinion dated Nov. 17, 2015, issued in counterpart Application No. PCT/JP2015/073769 (4 pages).
International Search Report dated Nov. 17, 2015, issued in Application No. PCT/JP2015/073769 (3 pages).
Non-Final OA dated Jun. 28, 2017, issued in U.S. Appl. No. 14/895,835 (19 pages).
Non-Final OA dated Jun. 30, 2017, issued in U.S. Appl. No. 15/316,980 (20 pages).
International Search Report dated Jul. 14, 2015, issued in counterpart International Application No. PCT/JP2015/061545 (4 pages).
Non-Final OA dated Jul. 3, 2017, issued in U.S. Appl. No. 15/305,822 (11 pages).
International Search Report dated Feb. 9, 2016, issued in counterpart Application No. PCT/JP2015/082841 (2 pages).
International Search Report dated Sep. 16, 2014, issued in counterpart Application No. PCT/JP2014/070419 (2 pages).
Office Action dated Mar. 14, 2017, issued in Chinese Application No. 201480033301.2, with partial English translation (11 pages).
Office Action dated Jun. 9, 2010, issued in counterpart Japanese Application No. 2005-064179 (2 pages).
International Search Report dated May 17, 2005, issued in Application No. PCT/JP2005/006138 (1 page).
Non-Final Office Action dated Mar. 4, 2009, issued in U.S. Appl. No. 10/594,587 (9 pages).
Final Office Action dated Nov. 27, 2009, issued in U.S. Appl. No. 10/594,587 (11 pages).
Non-Final OA dated Jun. 11, 2010, issued in U.S. Appl. No. 10/594,587 (6 pages).
Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Final Office Action dated Nov. 17, 2017, issued in U.S. Appl. No. 15/305,822 (9 pages).
Non-Final Office Action dated Dec. 19, 2017, issued in U.S. Appl. No. 15/309,510 (16 pages).
Non-Final Office Action dated Jan. 31, 2018, issued in U.S. Appl. No. 15/529,382 (25 Pages).
Non-Final Office Action dated Nov. 20, 2017, issued in U.S. Appl. No. 14/897,461 (27 pages).
Office Action dated Mar. 20, 2018, issued in counterpart Japanese Application No. 2014-087638, with English translation (9 pages).
Notice of Allowance dated May 1, 2018, issued in U.S. Appl. No. 14/897,461 (27 pages).
Notice of Allowance dated Apr. 27, 2018, issued in U.S. Appl. No. 15/309,510 (24 pages).
International Search Report dated Mar. 1, 2016, issued in counterpart International Application No. PCT/JP2015/082818 (2 pages).
International Search Report dated Jul. 14, 2015 issued in International Application No. PCT/JP2015/062244 (2 pages).
Non-Final Office Action dated Mar. 1, 2018, issued in U.S. Appl. No. 15/305,822 (7 pages).
Notice of Allowance dated Mar. 22, 2018, issued in U.S. Appl. No. 15/316,980 (18 pages).
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp (3 pages); cited in Non-Final Office Action dated Mar. 1, 2018 for U.S. Appl. No. 15/305,822.
Sylowhite SM 405, Jul. 2009, <http://novana.ch/news/8/3/0/sylowhite-sm-405> (1 page); cited in Non-Final Office Action dated Mar. 1, 2018 for U.S. Appl. No. 15/305,822.
English Translation of JP2002/303618, Oct. 2002; (14 pages); cited in Non-Final Office Action dated Mar. 1, 2018 for U.S. Appl. No. 15/305,822.
English Translation of JP 2004/101488, Apr. 2004 (9 pages); cited in Non-Final Office Action dated Mar. 1, 2018 for U.S. Appl. No. 15/305,822.
English Translation of WO 2014/038612, Mar. 2014 (10 pages); cited in Non-Final Office Action dated Mar. 1, 2018 for U.S. Appl. No. 15/305,822.
Janus Green B, no date available; https://pubchem.ncbi.nlm.nih.gov/compound/Janus_green_B< (17 pages); cited in Non-Final Office Action dated Mar. 1, 2018 for U.S. Appl. No. 15/305,822.
Final Office Action dated Nov. 17, 2017, issued in U.S. Appl. No. 15/305,822, (13 pages).
Final Office Action dated May 25, 2018, issued in U.S. Appl. No. 15/529,382 (37 pages).
Notice of Allowance dated Jun. 13, 2018, issued in U.S. Appl. No. 15/316,980 (19 pages).
Notice of Allowance dated Aug. 15, 2018, issued in U.S. Appl. No. 15/529,382 (16 pages).
Notice of Allowance dated Aug. 7, 2018, issued in U.S. Appl. No. 15/305,822 (18 pages).
Kitaoka, Kyozo, "Guide for Coatings to Synthetic Resin", May 25, 1974, First Edition, pp. 212-213, with English translation; Cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation; Cited in Japanese Office Action dated Aug. 21, 2018.
Office Action dated Aug. 21, 2018, issued in Japanese Application No. 2014-087638, with English translation (7 pages).
Notice of Allowance dated Sep. 6, 2018, issued in U.S. Appl. No. 15/309,510 (13 pages).
Office Action dated Sep. 28, 2010, issued in counterpart Japanese Application No. 2005-064179, with English translation (5 pages).
Office Action dated Mar. 26, 2013, issued in counterpart Japanese Application No. 2010-263654, with English translation (5 pages).
Office Action dated Dec. 4, 2018, issued in counterpart Japanese Application No. 2015-095244, with English translation (5 pages).
Office Action dated Jan. 2019, issued in U.S. Appl. No. 15/316,980 (7 pages).
Office Action dated Aug. 28, 2018, issued in counterpart Japanese Application No. 2015-532792, with English translation (6 pages).
Office Action dated Sep. 5, 2018, issued in counterpart Chinese Application No. 201580020478.3, with English translation (12 pages).
Office Action dated Oct. 9, 2018, issued in counterpart Japanese Application No. 2015-562838, with English translation (5 pages).
Office Action dated Oct. 9, 2018, issued in counterpart Japanese Application No. 2014-244414, with English translation (7 pages).
Office Action dated Dec. 25, 2018, issued in counterpart CN Application No. 201580007914.3, with English translation (15 pages).
Office Action dated Feb. 5, 2019, issued in counterpart JP Application No. 2015-532792, with English translation (9 pages).

* cited by examiner

PLASMA PROCESSING DETECTION INDICATOR

TECHNICAL FIELD

The present invention relates to a plasma treatment detection indicator. The plasma treatment as referred to herein means a plasma treatment using plasma generated by applying AC voltage, pulse voltage, high-frequency waves, microwaves, etc., to a gas for generating plasma. The plasma treatment includes both reduced-pressure plasma and atmospheric-pressure plasma.

BACKGROUND ART

Various types of equipment, instruments, etc., used in hospitals, laboratories, and the like are sterilized for disinfection and for killing bacteria and fungi. Plasma treatment is known as a sterilization treatment (see, for example, "3.3.1 Teiatsuryoku hoden purazuma wo mochiita mekkin jikken [3.3.1 Sterilization Experiment Using Low-pressure Discharge Plasma]" in Non-patent Literature 1).

Plasma treatment is used not only for sterilization treatment but also for plasma dry etching and plasma cleaning of the surface of items to be treated, such as electronic parts, in the process of producing semiconductor devices.

Plasma dry etching generally comprises applying high-frequency power to electrodes disposed in a reaction chamber that is a vacuum vessel, plasmarizing a gas for generating plasma introduced in the reaction chamber, and etching a semiconductor wafer with high precision. Plasma cleaning removes metal oxides, organic substances, burrs, etc., deposited on or adhering to the surface of items to be treated, such as electronic parts, to improve bonding or the wettability of solder, thus enhancing bonding strength and improving adhesion to a sealing resin and wettability.

A known method for detecting the completion of such plasma treatment is a method using a plasma treatment detection indicator in which a color-changing layer changes color in a plasma treatment atmosphere.

For example, Patent Literature 1 discloses an ink composition for detecting plasma treatment, the composition comprising 1) at least one member selected from the group consisting of anthraquinone colorants, azo colorants, and phthalocyanine colorants and 2) at least one member selected from the group consisting of binder resins, cationic surfactants, and extenders, a gas for generating plasma used for the plasma treatment containing at least one member selected from the group consisting of oxygen and nitrogen; and a plasma treatment detection indicator comprising a color-changing layer formed on a base material, the color-changing layer comprising the ink composition.

Patent Literature 2 discloses an ink composition for detecting inert gas plasma treatment, the composition comprising 1) at least one member selected from the group consisting of anthraquinone colorants, azo colorants, and methine colorants and 2) at least one member selected from the group consisting of binder resins, cationic surfactants, and extenders, the inert gas containing at least one member selected from the group consisting of helium, neon, argon, krypton, and xenon; and a plasma treatment detection indicator comprising a color-changing layer formed on a base material, the color-changing layer comprising the ink composition.

These plasma treatment detection indicators are useful indicators that allow the completion of plasma treatment to be determined by a change in the color of the color-changing layer. To enable the color change behavior of the color-changing layer to be determined with further certainty, a fibrous base material or a synthetic resin base material comprising a coloring pigment (hiding pigment) such as titanium dioxide, both of which are capable of hiding the color of the place on which they are disposed, is generally used as a base material.

However, when a fibrous base material or a synthetic resin base material comprising a coloring pigment is used, the surface of the base material may be affected by plasma in plasma treatment, causing fine fiber pieces or coloring pigment to be generated in a powder form. When such fine fiber pieces or coloring pigment is adhered to the color-changing layer, it may affect the accurate determination of a color change in the color-changing layer after plasma treatment.

Accordingly, development has been desired for a plasma treatment detection indicator that uses a fibrous base material or a synthetic resin base material comprising a coloring pigment as a base material and in which fine fiber pieces or coloring pigment is prevented from being generated in a powder form from the base material in plasma treatment.

CITATION LIST

Patent Literature

PTL 1: JP2013-098196A
PTL 2: JP2013-095764A

Non-Patent Literature

NPL 1: Journal of Plasma and Fusion Research Vol. 83, No. 7 Jul. 2007

SUMMARY OF INVENTION

Technical Problem

A primary object of the present invention is to provide a plasma treatment detection indicator that uses a fibrous base material or a synthetic resin base material comprising a coloring pigment as a base material and in which fine fiber pieces or coloring pigment is prevented from being generated in a powder form from the base material in plasma treatment.

Solution to Problem

The present inventor conducted extensive research to achieve the above object and found that the object can be achieved when the base material is covered with a specific transparent cover layer. The present invention has thus been accomplished.

Specifically, the present disclosure relates to the following plasma treatment detection indicator.

A plasma treatment detection indicator comprising a base material and at least a color-changing layer that changes color in a plasma treatment atmosphere, the color-changing layer being disposed above part or all of a surface of the base material, (1) the base material being a fibrous base material or a synthetic resin base material comprising a coloring pigment, and (2) a resin-based or inorganic transparent cover layer that covers all of the surface of the base material being disposed between the base material and the color-changing layer.

In the indicator according to another aspect of the present disclosure, the transparent cover layer has a thickness of 5 μm or more.

In the indicator according to yet another aspect of the present disclosure, the color-changing layer comprises a color-changing colorant that exhibits a change in chemical structure in a plasma treatment atmosphere to change color, and a non-color-changing colorant that does not exhibit a change in chemical structure in a plasma treatment atmosphere.

In the indicator according to yet another aspect of the present disclosure, the indicator comprises a non-color-changing layer between the base material and the transparent cover layer, the non-color-changing layer comprising a non-color-changing colorant that does not exhibit a change in chemical structure in a plasma treatment atmosphere.

In the indicator according to yet another aspect of the present disclosure, the non-color-changing layer and the color-changing layer are laminated in such a manner that the color-changing layer is placed above the non-color-changing layer so that their perimeters are aligned, with the transparent cover layer interposed therebetween.

Advantageous Effects of Invention

The plasma treatment detection indicator of the present invention uses a fibrous base material or a synthetic resin base material comprising a coloring pigment as a base material. Since the indicator of the present invention comprises, between the base material and the color-changing layer, a resin-based or inorganic transparent cover layer that covers all of the surface of the base material on the side on which the color-changing layer is laminated, the direct influence (etching effect) of plasma on the base material is mitigated even in a portion on which the color-changing layer is not formed. This prevents fine fiber pieces or coloring pigment from being generated in a powder form from the base material, enabling a color change in the color-changing layer after plasma treatment to be more precisely determined. Moreover, when the color-changing layer is formed above all of a surface of the base material and when the completion of plasma treatment is determined by the disappearance of the color-changing layer (disappearance due to the etching effect) in addition to a color change in the color-changing layer, the direct influence of plasma on the base material is mitigated also after the disappearance of the color-changing layer, thus preventing fine fiber pieces or coloring pigment from being generated in a powder form from the base material.

Since the plasma treatment detection indicator of the present invention comprises the transparent cover layer, the direct influence of plasma on the base material is mitigated. Thus, the plasma treatment detection indicator of the present invention also has an excellent effect such that the occurrence of curling and color change in the base material due to plasma treatment can be prevented.

These effects can be obtained both in the case of using reduced-pressure plasma as the plasma treatment and in the case of using atmospheric-pressure plasma as the plasma treatment.

DESCRIPTION OF EMBODIMENTS

Figure 1:
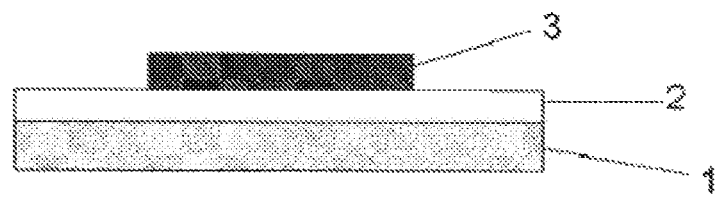
FIG. 1 illustrates an embodiment of the plasma treatment detection indicator of the present invention.

The plasma treatment detection indicator of the present invention is described in detail below.

The plasma treatment detection indicator (hereinafter referred to as "indicator") of the present invention comprises a base material and at least a color-changing layer that changes color in a plasma treatment atmosphere, the color-changing layer being disposed above part or all of a surface of the base material, (1) the base material being a fibrous base material or a synthetic resin base material comprising a coloring pigment, (2) a resin-based or inorganic transparent cover layer that covers all of the surface of the base material being disposed between the base material and the color-changing layer.

The indicator of the present invention, which has the above features, uses a fibrous base material or a synthetic resin base material comprising a coloring pigment, as a base material. Since the indicator of the present invention comprises, between the base material and the color-changing layer, a resin-based or inorganic transparent cover layer that covers all of the surface of the base material on the side on which the color-changing layer is laminated, the direct influence (etching effect) of plasma on the base material is mitigated even in a portion on which the color-changing layer is not formed. This prevents fine fiber pieces or coloring pigment from being generated in a powder form from the base material, enabling the color change in the color-changing layer after plasma treatment to be more precisely determined. Moreover, when the color-changing layer is formed above all of a surface of the base material and when the completion of plasma treatment is determined by the disappearance of the color-changing layer (disappearance due to the etching effect) in addition to color change in the color-changing layer, the direct influence of plasma on the base material is mitigated also after disappearance of the color-changing layer, thus preventing fine fiber pieces or coloring pigment from being generated in a powder form from the base material.

In addition, since the direct influence of plasma on the base material is mitigated by virtue of the transparent cover layer of the plasma treatment detection indicator of the present invention, the plasma treatment detection indicator of the present invention also has an excellent effect such that occurrence of curling and color change of the base material due to plasma treatment can be prevented.

These effects can be obtained both in the case of using reduced-pressure plasma as the plasma treatment and in the case of using atmospheric-pressure plasma as the plasma treatment.

Base Material

The indicator of the present invention uses a fibrous base material or a synthetic resin base material comprising a coloring pigment as a base material. There is no limitation on the shape of the base material. The base material is generally in the shape of a sheet or a film.

The base material used in the present invention has properties that hide the color of the place on which the indicator is disposed. The fibrous base material is generally opaque, and the coloring pigment is a hiding pigment.

Examples of fibrous base materials include paper (high-quality paper, coated paper, synthetic paper), fibers (non-woven fabric, woven fabric, other fibrous sheet), composite materials thereof, and the like. Examples of synthetic paper include synthetic resin fiber paper, such as polypropylene synthetic paper and polyethylene synthetic paper.

Examples of resins that can be used for the synthetic resin base material include synthetic resins, such as polypropylenes, polyvinyl chlorides, polyesters (e.g, polyethylene terephthalate and polyethylene naphthalate), polystyrenes, polyethylenes, polyimides, polyamides, polycarbonates, and polyacrylonitriles. These synthetic resins may be used singly or in a combination of two or more. Among these synthetic resins, at least one member selected from the group consisting of polyethylene terephthalate, polyethylene naphthalate, polyethylenes, polyimides, and polypropylenes is particularly preferable.

The coloring pigment contained in the synthetic resin base material is not particularly limited as long as it can hide the color of the place on which the indicator is disposed. The type and amount of coloring pigment can be appropriately set according to usage conditions of the indicator. When the base material is white, examples of the type of coloring pigment include titanium dioxide, calcium carbonate, zinc oxide, and like coloring pigments. The particle size of the coloring pigment is about 0.1 to 10 µm. In general, a wide variety of commercially available colored synthetic resin sheets can be used.

There is no limitation on the thickness of the base material. The thickness of the base material is preferably about 0.1 to 0.5 mm.

Resin-Based or Inorganic Transparent Cover Layer

The indicator of the present invention comprises a resin-based or inorganic transparent cover layer that covers all of the surface of the base material on the side on which the color-changing layer is laminated. Thus, the direct influence (etching effect) of plasma on the base material is mitigated even in a portion on which the color-changing layer is not formed, thus preventing fine fiber pieces or coloring pigment from being generated in a powder form from the base material. As described later, a non-color-changing layer that does not change color in a plasma treatment atmosphere may be disposed between the base material and the transparent cover layer, if necessary. Embodiments of the present invention are described below with reference to examples shown in FIGS. 1 and 2.

Figure 2:
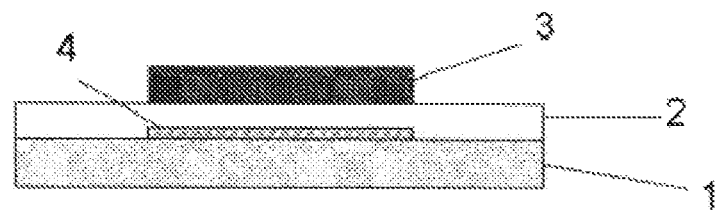
FIG. 2 illustrates an embodiment of the plasma treatment detection indicator of the present invention.

FIG. 1 illustrates an embodiment in which a color-changing layer 3 is disposed above part of a surface (one side) of a base material 1. Between the base material 1 and the color-changing layer 3, a transparent cover layer 2 that covers all of the surface (one side) of the base material 1 is formed. FIG. 2 illustrates an embodiment in which a color-changing layer 3 is disposed above part of a surface (one side) of a base material 1. Between the base material 1 and the color-changing layer 3, a transparent cover layer 2 that covers all of the surface (one side) of the base material 1 is formed. Further, between the base material 1 and the transparent cover layer 2, a non-color-changing layer 4 having the same perimeter as that of the color-changing layer 3 is formed in such a manner that the color-changing layer 3 is placed above the non-color-changing layer 4 (aligned). As shown in FIGS. 1 and 2, "between the base material 1 and the color-changing layer 3" includes not only a region directly sandwiched between the base material 1 and the color-changing layer 3, but also a region that is on the surface of the base material 1 and on which the color-changing layer 3 is not laminated.

Examples of the method for forming the transparent cover layer that covers the base material include 1) a method in which a resin-based or inorganic film that serves as a transparent cover layer is laminated on a surface of a base material (in the case where a non-color-changing layer is formed, the surfaces of the base material and the non-color-changing layer); 2) a method in which a coating liquid for forming a resin-based or inorganic transparent cover layer is applied to a surface of a base material (in the case where a non-color-changing layer is formed, the surfaces of the base material and the non-color-changing layer), and the coating film is cured; and the like.

Examples of method 1) described above, which comprises laminating a resin-based or inorganic film that serves as a transparent cover layer, include methods in which a resin-based film or an inorganic film is laminated using, as necessary, a known adhesive. Examples of resin-based films include polypropylenes, polyvinyl chlorides, polyesters (e.g., polyethylene terephthalate and polyethylene naphthalate), polystyrenes, polyethylenes, polyimides, polyamides, polycarbonates, polyacrylonitriles, and the like. Examples of inorganic films include glass and the like. The type and amount of adhesive can be appropriately selected according to the materials of the base material and the transparent cover layer.

Examples of method 2) described above, which comprises applying a coating liquid for forming a resin-based or inorganic transparent cover layer and curing the coating film, include methods such as the following evaporation drying type, emulsion type, oxidation polymerization type, heat curing type, and photo-curing type according to the type of coating liquid or curing method. In the embodiments described below, the application conditions and the curing conditions are not limited and can be appropriately set according to the desired thickness of the transparent cover layer and the type of coating liquid.

Examples of evaporation drying type methods include those in which, for example, a solution obtained by dissolving one or more members selected from the group consisting of rosin, shellac, casein, rosin-maleic acid resins, alkyd resins, cellulose derivatives, petroleum resins, low molecular weight polyethylenes, polystyrenes, polyvinyl acetates, vinyl chloride-vinyl acetate copolymers, polyacrylic acid ester-based coplymers, modified rubbers, polyvinyl alcohol, polyvinylpyrrolidones, and the like in a petroleum-based solvent, an aromatic solvent, an aliphatic hydrocarbon-based solvent, an alcohol-based solvent, a ketone-based solvent, an ester-based solvent, or water is applied to a base material and dried and cured. Examples also include those in which an aqueous solution of sodium silicate (water glass) is applied to a base material and dried and cured.

Examples of emulsion type methods include those in which a polyvinyl acetate-based, styrene-butadiene-based, or acrylic emulsion is applied to a base material and dried and cured.

Examples of oxidation polymerization type methods include those in which, for example, a drying oil, such as polymerized linseed oil, tung oil, or dehydrated castor oil, and an oil-modified alkyd resin, such as a soybean oil-modified alkyd resin, a coconut oil-modified alkyd resin, or a linseed oil-modified alkyd resin are applied to a base material and subjected to oxidation polymerization curing.

Examples of heat curing type methods include those in which an epoxy resin, an alkyd resin, an acrylic resin, a xylene resin, a guanamine resin, a phenolic resin, an unsaturated polyester resin, a polyurethane resin, a maleic acid resin, a melamine resin, a urea resin, or the like is applied to a base material and thermally cured.

Examples of photo-curing type methods include those in which a photopolymerizable acrylic acid-based resin, a photocurable epoxy resin, a water-soluble synthetic resin coating composition, a water-soluble alkyd resin, a water-soluble melamine resin, a water-soluble urea resin, a water-soluble phenolic resin, a water-soluble acrylic resin, a water-soluble epoxy resin, a water-soluble polybutadiene resin, or the like is applied to a base material and photocured.

Among these, polyester-based resins, thermosetting resins, or photocuring resins are particularly preferable.

There is no limitation on the thickness of the transparent cover layer. The thickness of the transparent cover layer is preferably 5 μm or more, and more preferably about 8 to 30 μm. In particular, the transparent cover layer preferably has a thickness of about 10 to 25 μm. Since the thickness is 5 μm or more, the direct influence of plasma on the base material can be mitigated with further certainty.

Color-Changing Layer

The indicator of the present invention comprises a color-changing layer on the transparent cover layer. The color-changing layer changes color in a plasma treatment atmosphere using a gas for generating plasma. The region where the color-changing layer is formed may be part or all relative to a surface of the base material. FIGS. 1 and 2 show examples of an embodiment in which the color-changing layer is partially formed relative to a surface of the base material. The color-changing layer can be disposed on one or both sides of the base material. As shown in FIGS. 1 and 2, the color-changing layer is generally disposed on one side of the base material.

The term "color-changing" in the color-changing layer includes a change to other colors and also includes color fading or decolorization. The method for confirming the completion of plasma treatment by a change in the color-changing layer is not limited to a method in which the completion of plasma treatment is determined by a color change in the color-changing layer, and also includes a method in which the completion of plasma treatment is confirmed by the disappearance of the color-changing layer eventually as a result of gradual thinning of the color-changing layer due to the etching effect of plasma. In this case, to accurately determine after the disappearance of the color-changing layer where the color-changing layer was formed, an embodiment in which a non-color-changing layer is formed under the transparent cover layer in such a manner that the non-color-changing layer is aligned with the color-changing layer is useful (FIG. 2).

The color-changing layer that changes color in a plasma treatment atmosphere using a gas for generating plasma can be formed by applying and drying an ink composition comprising a coloring agent that exhibits a change in chemical structure in a plasma treatment atmosphere to change color (referred to as "color-changing colorant" in the present specification). A wide variety of known ink compositions can be used as the ink composition. For instance, an ink composition comprising, for example, the following coloring agent, binder resin, surfactant, and other additives can be suitably used. Typical components contained in the ink composition are described below by way of example.

Coloring Agent

There is no limitation on the color-changing layer for detecting plasma, and the color-changing layer is suitably formed, for example, by using an ink composition comprising at least one coloring agent (color-changing colorant) selected from the group consisting of anthraquinone colorants, azo colorants, methine colorants, phthalocyanine colorants, leuco colorants (colorants having a lactone ring in the molecule), nitroso colorants, nitro colorants, azoic colorants (diazo components), azoic colorants (coupling components), stilbene colorants, carotenoid colorants, diarylmethane colorants, triarylmethane colorants, xanthene colorants, acridine colorants, quinoline colorants, thiazole colorants, indamine colorants, indophenol colorants, azine colorants, oxazine colorants, thiazine colorants, sulfur colorants, lactone colorants, hydroxyketone colorants, aminoketone colorants, indigoid colorants, natural colorants, and oxidized colorants. These colorants (including dyes) are color-changing colorants that exhibit a change in chemical structure in a plasma treatment atmosphere to change color, and may be used singly or in a combination of two or more. Preferred among these color-changing colorants is at least one member selected from the group consisting of anthraquinone colorants, azo colorants, methine colorants, and phthalocyanine colorants.

The anthraquinone colorants may be any colorant that has anthraquinone as a basic skeleton. Known anthraquinone dispersing dyes and the like are also usable. In particular, anthraquinone colorants containing an amino group are preferable. Anthraquinone colorants containing at least one amino group selected from the group consisting of primary amino groups and secondary amino groups are more preferable. In this case, the anthraquinone colorants may contain one or more primary amino groups and/or one or more secondary amino groups, and each of the amino groups may be of the same or different type.

Specific examples include 1,4-diaminoanthraquinone (C.I. Disperse Violet 1), 1-amino-4-hydroxy-2-methylaminoanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraminoanthraquinone (C.I. Disperse Blue 1), 1,4-diamino-5-nitroanthraquinone (C.I. Disperse Violet 8), and the like (color index names are in parentheses).

Other usable colorants include those known as C.I. Solvent Blue 14, C.I. Solvent Blue 35, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19, C.I. Disperse Blue 7, and the like.

These anthraquinone colorants may be used singly or in a combination of two or more. Among these anthraquinone colorants, C.I. Disperse Blue 7, C.I. Disperse Violet 1, and the like are preferable. In the present invention, detection sensitivity can be controlled by changing the kinds (molecular structures, etc.) of such anthraquinone colorants used.

The azo colorants may be any colorant that has azo-N=N— as a chromophore. Examples of such colorants include monoazo colorants, polyazo colorants, metal complex azo colorants, stilbene azo colorants, thiazole azo colorants, and the like. As indicated by color index names, specific examples of such colorants include C.I. Solvent Red 1, C.I. Solvent Red 3, C.I. Solvent Red 23, C.I. Disperse Red 13, C.I. Disperse Red 52, C.I. Disperse Violet 24, C.I. Disperse Blue 44, C.I. Disperse Red 58, C.I. Disperse Red 88, C.I. Disperse Yellow 23, C.I. Disperse Orange 1, C.I. Disperse Orange 5, C.I. Disperse Red 167:1, and the like. These colorants may be used singly or in a combination of two or more.

The methine colorants may be any colorant that has a methine group. Polymethine colorants, cyanine colorants, and the like are thus also included within the scope of methine colorants in the present invention. These colorants can be appropriately selected from known or commercially available methine colorants. Specific examples include C.I.

Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 11, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, C.I. Basic Blue 62, C.I. Basic Blue 63, and the like. These colorants may be used singly or in a combination of two or more.

The phthalocyanine colorants may be any colorant that has a phthalocyanine structure. Examples of such colorants include blue copper phthalocyanine, greenish blue metal-free phthalocyanine, green highly chlorinated phthalocyanine, yellowish green poorly chlorinated phthalocyanine (brominated chlorinated copper phthalocyanine), and the like. Specific examples of such colorants include C.I. Pigment Green 7, C.I. Pigment Blue 15, C.I. Pigment Blue 15:3, C.I. Pigment Blue 15:4, C.I. Pigment Blue 15:6, C.I. Pigment Blue 16, C.I. Pigment Green 36, C.I. Direct Blue 86, C.I. Basic Blue 140, C.I. Solvent Blue 70, and the like. These colorants may be used singly or in a combination of two or more.

In addition to the general phthalocyanine colorants mentioned above, other phthalocyanine colorants are also usable. Examples of such colorants include compounds that have as central metal(s) at least one metal selected from the group consisting of zinc, iron, cobalt, nickel, lead, tin, manganese, magnesium, silicon, titanium, vanadium, aluminum, iridium, platinum, and ruthenium, with the central metal(s) being coordinated with phthalocyanine; such compounds in which the central metal(s) are bonded to oxygen or chlorine and are coordinated with phthalocyanine; and the like.

The content of the coloring agent can be appropriately determined according to the type of coloring agent, the desired hue, etc. The content of the coloring agent in the ink composition is generally preferably about 0.05 to 5 wt %, and particularly preferably 0.1 to 1 wt %.

In the present invention, colorants and pigments other than the coloring agents mentioned above may also be present. In particular, a coloring agent that does not exhibit a change in chemical structure in a plasma treatment atmosphere (referred to as "non-color-changing colorant" in the present specification) may be used. This enables the visual recognition effect to be further enhanced by visualizing color tone changes from one color to another. The non-color-changing colorant may be a known ink (normal color ink). In this case, the content of the non-color-changing colorant can be appropriately set according to the type of non-color-changing colorant, etc. The non-color-changing colorant encompasses pigments that do not exhibit a change in chemical structure in a plasma treatment atmosphere.

The ink composition preferably comprises, in addition to the coloring agent mentioned above, at least one member selected from the group consisting of binder resins, nonionic surfactants, cationic surfactants and extenders.

Binder Resin

The binder resin may be suitably selected according to the type of surface to which the ink composition is applied (transparent cover layer). For example, known resin components used in ink compositions for writing, printing, etc., can be used. Specific examples include maleic resins, ketone resins, alkylphenol resins, rosin modified resins, polyvinyl butyral, cellulosic resins, polyester-based resins, styrene maleic resins, styrene acrylic acid resins, acrylic resins, and the like. These binder resins may be used singly or in a combination of two or more.

Cellulosic resins are particularly preferable for use in the present invention. Use of a cellulosic resin can impart excellent fixing properties even when the ink composition contains an extender (e.g., silica), and can efficiently prevent, for example, falling and detachment from the transparent cover layer. Efficiently producing cracks on the surface of the coating film of the ink composition can help enhance the sensitivity of the indicator.

In the present invention, the binder resins may be all or partially nitrogen-containing polymers other than the resins mentioned above. The nitrogen-containing polymers function as sensitivity enhancers as well as binders. Specifically, use of such a sensitivity enhancer can further enhance the accuracy (sensitivity) of plasma treatment detection.

Examples of usable nitrogen-containing polymers include synthetic resins, such as polyamide resins, polyimide resins, polyacrylonitrile resins, amino resins, polyacrylamides, polyvinylpyrrolidones, polyvinylimidazoles, and polyethyleneimines. These resins may be used singly or in a combination of two or more. Polyvinylpyrrolidones are preferable for use in the present invention. The type, molecular weight, etc., of polyamide resin are not particularly limited. Known or commercially available polyamide resins can be used. Among these, a polyamide resin that is a reaction product of a dimer of linoleic acid with a diamine or polyamine (a long-chain linear polymer) is suitable for use. Polyamide resins are thermoplastic resins that have a molecular weight of 4000 to 7000. Commercially available products can be used as such resins.

The content of the binder resin can be appropriately determined according to the types of binder resin and coloring agent used, etc. The content of the binder resin in the ink composition is generally preferably about 50 wt % or less, and particularly preferably 5 to 35 wt %. When the nitrogen-containing polymer is used as a binder resin, the content of the nitrogen-containing polymer in the ink composition is preferably about 0.1 to 50 wt %, and particularly preferably 1 to 20 wt %.

Nonionic Surfactant

The nonionic surfactant functions as a color change accelerator. Using the nonionic surfactant with a coloring agent can provide more excellent detection sensitivity.

The nonionic surfactant is at least one member selected from the group consisting of nonionic surfactants represented by formulae (I) to (V).

The nonionic surfactants represented by formula (I)

$$R_1—X-(AO)_n—R_2 \qquad (I)$$

(wherein $R_1$ and $R_2$ are each independently hydrogen or a straight-chain or branched aliphatic hydrocarbon group having 1 to 30 carbon atoms; X is oxygen or an ester bond; AO is a repeating unit derived from an alkylene oxide; and n is an integer of 1 to 200) are alkylene glycol derivatives.

The nonionic surfactants represented by formula (II)

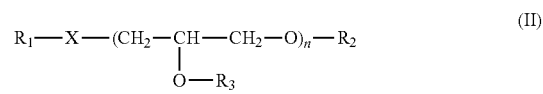

$$R_1—X—(CH_2—CH—CH_2—O)_n—R_2 \\ \qquad\quad | \\ \qquad\quad O—R_3 \qquad (II)$$

(wherein $R_1$, $R_2$, and $R_3$ are each independently hydrogen or a straight-chain or branched aliphatic hydrocarbon group having 1 to 30 carbon atoms; X is oxygen or an ester bond; and n is an integer of 1 to 200) are polyglycerin derivatives.

In formula (I), examples of AO (monomer) include ethylene oxide, propylene oxide, 1,2-butylene oxide, 2,3-butylene oxide, tetrahydrofuran, styrene oxide, and the like. The form of polymerization of AO may be a homopolymer, or a block copolymer or a random copolymer of two or more kinds of AO. In formulae (I) and (II), "having 1 to 30 carbon atoms" refers to preferably having 1 to 22 carbon atoms, and more preferably having 10 to 18 carbon atoms. X is preferably oxygen, and n is preferably an integer of 1 to 100.

Specific examples of nonionic surfactants represented by the above formula (I) or (II) include polyethylene glycols (for example, the commercially available product "PEG2000" produced by Sanyo Chemical Industries, Ltd.), glycerin, polyethylene glycol-polypropylene glycol copolymers (for example, the commercially available product "Span 710" produced by DKS Co. Ltd.), and the like.

In the above, polymers wherein at least one of $R_1$ and $R_2$ is substituted with a straight-chain or branched aliphatic hydrocarbon group having 1 to 30 carbon atoms are also preferable.

Specific examples include polyoxyethylene (hereinafter "POE") lauryl ethers (for example, the commercially available product "Emulgen 109P"), POE cetyl ethers (for example, the commercially available product "Emulgen 220"), POE oleyl ethers (for example, the commercially available product "Emulgen 404"), POE stearyl ethers (for example, the commercially available product "Emulgen 306"), and POE alkyl ethers (for example, the commercially available product "Emulgen LS-110") (all produced by Kao Corporation); POE tridecyl ethers (for example, the commercially available product "Fine Serve TD-150") and polyethylene glycol monostearates (for example, the commercially available product "Blaunon S-400A") (both produced by Aoki Oil Industrial Co., Ltd.); polyethylene glycol monooleates (for example, the commercially available product "Nonion O-4"), tetramethylene glycol derivatives (for example, the commercially available product "Polycerin DC-1100"), polybutylene glycol derivatives (for example, the commercially available product "Uniol PB-500"), and alkylene glycol derivatives (for example, the commercially available product "Unilube 50MB-5") (all produced by NOF Corporation); POE (20) octyldodecyl ethers (for example, the commercially available product "Emalex OD-20") and POE(25) octyldodecyl ethers (for example, the commercially available product "Emalex OD-25") (both produced by Nihon Emulsion Co., Ltd.); and the like.

The nonionic surfactants represented by formulae (III) and (IV)

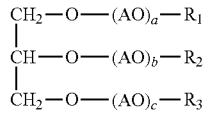

(III)

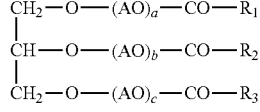

(IV)

(wherein $R_1$, $R_2$, and $R_3$ are each independently hydrogen or a straight-chain or branched aliphatic hydrocarbon group having 1 to 30 carbon atoms; AO is a repeating unit derived from an alkylene oxide; and the sum of a, b, and c is an integer of 3 to 200) are alkylene glycol glyceryl derivatives.

In both of the above formulae, examples of AO (monomer) include ethylene oxide, propylene oxide, 1,2-butylene oxide, 2,3-butylene oxide, tetrahydrofuran, styrene oxide, and the like. The form of polymerization of AO may be a homopolymer, or a block copolymer or a random copolymer of two or more kinds of AO. In both of the above formulae, "having 1 to 30 carbon atoms" refers to preferably having 1 to 22 carbon atoms, and more preferably having 10 to 18 carbon atoms, and the sum of a, b, and c is preferably an integer of 3 to 50.

Examples of nonionic surfactants represented by formula (III) include compounds wherein $R_1$ is an isostearic acid residue, $R_2$ and $R_3$ are hydrogen, and AO (monomer) is ethylene oxide. Specific examples include POE glyceryl isostearates (for example, the commercially available product "Uniox GM-30IS" produced by NOF Corporation).

Examples of nonionic surfactants represented by formula (IV) include compounds wherein $R_1$ to $R_3$ are isostearic acid residues, and AD (monomer) is ethylene oxide. Specific examples include POE glyceryl triisostearates (for example, the commercially available product "Uniox GT-30IS" produced by NOF Corporation).

The nonionic surfactants represented by formula (V)

$$R_1-X-(AO)_p-R_2-C\equiv C-R_3-X-(AO)_q-R_4 \quad (V)$$

(wherein $R_1$, $R_2$, $R_3$, and $R_4$ are each independently hydrogen or a straight-chain or branched aliphatic hydrocarbon group having 1 to 30 carbon atoms; is oxygen or an ester bond; AO is a repeating unit derived from an alkylene oxide; and the sum of p and q is an integer of 0 to 20) are acetylene glycol derivatives.

In formula (V), examples of AO (monomer) include ethylene oxide, propylene oxide, 1,2-butylene oxide, 2,3-butylene oxide, tetrahydrofuran, styrene oxide, and the like. The polymerization form of AO includes a homopolymer, or a block copolymer or a random copolymer of two or more kinds of AO. In formula (V), "having 1 to 30 carbon atoms" refers to preferably having 1 to 22 carbon atoms, X is preferably oxygen, and the sum of p and p is preferably an integer of 0 to 10.

Examples of nonionic surfactants represented by formula (V) include compounds wherein $R_1$ and $R_4$ are hydrogen, $R_2$ and $R_3$ are $>C(CH_3)(i-C_4H_9)$, X is oxygen, and the sum of p and p is 0. Specific examples include 2,4,7,9-tetramethyl-5-decyne-4,7-diol (for example, the commercially available product "Surfynol 104H" produced by Air Products Japan, Inc.).

The nonionic surfactants represented by formulae (I) to (V) may be used singly or in a combination of two or more.

The content of the nonionic surfactant can be suitably determined according to the types of nonionic surfactant and coloring agent used, etc. In consideration of the preservability in the composition and color-change-accelerating effect, the content of the nonionic surfactant in the ink composition is generally preferably about 0.2 to 10 wt %, and particularly preferably 0.5 to 5 wt %.

Cationic Surfactant

The cationic surfactant is not particularly limited. At least one member selected from the group consisting of tetraalkylammonium salts, isoquinolinium salts, imidazolinium salts, and pyridinium salts is particularly preferable. These cationic surfactants may be commercially available products. Using such a cationic surfactant with the coloring agent mentioned above can provide more excellent detection sensitivity. The above cationic surfactants may be used singly or in a combination of two or more.

Among tetraalkylammonium salts, alkyltrimethylammonium salts, dialkyldimethylammonium salts, and the like are preferable. Specific examples include coconut alkyltrimethylammonium chloride, tallow alkyltrimethylammonium chloride, behenyltrimethylammonium chloride, myristyl trimethylammonium chloride, tetramethylammonium chloride, tetrabutylammonium chloride, tetrapropylammonium chloride, tetramethylammonium bromide, tetrabutylammonium bromide, tetrapropylammonium bromide, trimethyl-2-hydroxyethylammonium chloride, cetyltrimethylammonium chloride, lauryltrimethylammonium chloride, stearyltrimethylammonium chloride, dioctyldimethylammonium chloride, distearyldimethylammonium chloride, alkylbenzyldimethylammonium chloride, and the like. In particular, behenyltrimethylammonium chloride, lauryltrimethylammonium chloride, and the like are preferable.

Examples of isoquinolinium salts include lauryl isoquinolinium bromide, cetyl isoquinolinium bromide, cetyl isoquinolinium chloride, lauryl isoquinolinium chloride, and the like. Among these, lauryl isoquinolinium bromide is particularly preferable.

Examples of imidazolinium salts include 1-hydroxyethyl-2-oleylimidazolinium chloride, 2-chloro-1,3-dimethylimidazolinium chloride, and the like. Among these, 2-chloro-1,3-dimethylimidazolinium chloride is particularly preferable.

Examples of pyridinium salts include pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-1-methylpyridinium iodide, 3,4-dimethylbutylpyridinium chloride, pyridinium-n-hexadecyl chloride-hydrate, N-(cyanomethyl)pyridinium chloride, N-acetonylpyridinium bromide, 1-(aminoformylmethyl)pyridinium chloride, 2-amidinopyridinium chloride, 2-aminopyridinium chloride, N-aminopyridinium iodide, 1-aminopyridinium iodide, 1-acetonylpyridinium chloride, N-acetonylpyridinium bromide, and the like. Among these, hexadecylpyridinium chloride is particularly preferable.

The content of the cationic surfactant can be suitably determined according to the types of cationic surfactant and coloring agent used, etc. The content of the cationic surfactant in the ink composition is generally preferably about 0.2 to 10 wt %, and particularly preferably 0.5 to 5 wt %.

Extender

The extender is not particularly limited. Examples of extenders include bentonite, activated clay, aluminum oxide, silica, silica gel, and like inorganic materials. Materials known as extender pigments can also be used. Among these, at least one member selected from the group consisting of silica, silica gel, and alumina is preferable, and silica is particularly preferable. When silica or the like is used, cracks can be particularly effectively produced on the surface of the color-changing layer. As a result, the detection sensitivity of the indicator can be further increased. These extenders may be used singly or in a combination of two or more.

The content of the extender can be suitably determined according to the types of extender and coloring agent used, etc. The content of the extender in the ink composition is generally preferably about 1 to 30 wt %, and particularly preferably 2 to 20 wt %.

Other Additives

If required, the ink composition may appropriately contain components used in known inks, such as solvents, photo-polymerization initiators, leveling agents, antifoaming agents, ultraviolet absorbers, and surface conditioners.

Solvents that can be used in the present invention may be any solvent that is generally used in ink compositions for printing, writing, etc. Various solvents can be used, such as alcohol-based, polyhydric alcohol-based, ester-based, ether-based, ketone-based, hydrocarbon-based, and glycol ether-based solvents. The solvent to be used can be suitably selected in consideration of the solubility of the colorant and binder resin used, etc. These solvents may be used singly or in a combination of two or more.

The content of the solvent can be suitably determined according to the types of solvent and coloring agent used, etc. The content of the solvent in the ink composition is generally preferably about 40 to 95 wt %, and particularly preferably 60 to 90 wt %.

Photo-polymerization initiators that can be used in the present invention are not particularly limited as long as they act as color change accelerators that improve the speed of the color change of colorants (including dyes) contained in the color-changing layer in a plasma treatment atmosphere. Using such a photo-polymerization initiator in combination can provide excellent detection sensitivity and enables the speed of color change to be controlled by adjusting the content of the photo-polymerization initiator.

Although the detailed reason why photo-polymerization initiators act as color change accelerators is unknown, photo-polymerization initiators are considered to generate radicals in a plasma treatment atmosphere to change the structures of colorants (such as partial decomposition or bond cleavage), thereby exhibiting a color-change-accelerating effect.

There is no limitation on the photo-polymerization initiator. For example, preferred is at least one member selected from the group consisting of alkylphenone-based photo-polymerization initiators, acylphosphine oxide-based photo-polymerization initiators, titanocene-based photo-polymerization initiators, acetophenone-based photo-polymerization initiators, benzophenone-based photo-polymerization initiators, thioxanthone-based photo-polymerization initiators, cationic photo-polymerization initiators, and anionic photo-polymerization initiators. More preferred among these photo-polymerization initiators is at least one member selected from the group consisting of alkylphenone-based photo-polymerization initiators and acylphosphine oxide-based photo-polymerization initiators.

The content of the photo-polymerization initiator can be suitably determined according to the types of photo-polymerization initiator and colorant used. In consideration in the preservability of the ink composition and the color-change-accelerating effect, the content of the photo-polymerization initiator in the ink composition is generally preferably about 0.05 to 20 wt %, and particularly preferably 1 to 10 wt %. If the content of the photo-polymerization initiator is more than 20 wt %, the photo-polymerization initiator may not be dissolved completely in the ink composition. If the content of the photo-polymerization initiator is less than 0.05 wt %, the color-change-accelerating effect may not be exhibited sufficiently.

The components of the ink composition of the present invention may be added all at once or sequentially, and mixed uniformly by using a known stirrer, such as a homogenizer or a dissolver. For example, first the coloring agent mentioned above and at least one member selected from the group consisting of binder resins, cationic surfactants, and extenders (other additives as required) may be sequentially added to a solvent, and the resultant mixture may be mixed and stirred using a stirrer.

Method for Forming Color-Changing Layer

The color-changing layer can be formed using the ink composition mentioned above according to a known printing method, such as spin coating, slit coating, sol-gel method, spraying, silk screen printing, gravure printing, offset printing, relief printing, flexographic printing; a known coating method; or the like.

The color-changing layer preferably has cracks on the surface. Specifically, the color-changing layer preferably has open pores formed on the surface thereof and is porous. With this structure, the detection sensitivity in plasma treatment can be further enhanced. In this case, the desired color change effect can be obtained even when the color-changing layer is disposed in the plasma treatment detection indicator. Cracks can be effectively formed especially by using a cellulosic resin as a binder resin for the ink composition of the present invention. Specifically, use of a cellulosic resin enables the formation of cracks as mentioned above, while maintaining good fixing properties.

There is no limitation on the thickness of the color-changing layer. The thickness of the color-changing layer is generally about 1 to 10 μm.

Non-Color-Changing Layer

In the present invention, a non-color-changing layer comprising a non-color-changing colorant that does not exhibit a change in chemical structure in a plasma treatment atmosphere may be formed between the base material and the transparent cover layer. An embodiment in which the non-color-changing layer is provided separately from the color-changing layer or an embodiment in which a non-color-changing colorant in addition to a color-changing colorant is added to the color-changing layer may be alternatively selected. However, in the embodiment in which the non-color-changing layer is formed between the base material and the transparent cover layer, the influence of plasma on color fading of the non-color-changing layer (physical color fading due to the etching effect) can be mitigated; therefore, the embodiment in which the non-color-changing layer is formed separately from the color-changing layer between the base material and the transparent resin layer is preferable in the present invention.

The non-color-changing layer can generally be formed by using a commercially available normal color ink. Examples of usable inks include water-based inks, oil-based inks, solventless inks, and the like. The ink for use in the formation of the non-color-changing layer may contain components used in known inks, such as resin binders, extenders, and solvents.

The non-color-changing layer may be formed in the same manner as the formation of the color-changing layer. For example, the non-color-changing layer can be formed by using a normal color ink according to a known printing method, such as silk screen printing, gravure printing, offset printing, relief printing, or flexographic printing.

In the present invention, the color-changing layer and the non-color-changing layer may be freely combined as long as the completion of plasma treatment can be confirmed. For example, the color-changing layer and the non-color-changing layer can be formed in such a manner that the color difference between the color-changing layer and the non-color-changing layer can be recognized only after the color of the color-changing layer changes, or in such a manner that the color difference between the color-changing layer and the non-color-changing layer disappears only after the color of the color-changing layer changes. The completion of plasma treatment may also be confirmed by the disappearance of the color-changing layer and the exposure of the non-color-changing layer eventually as a result of the gradual thinning of the color-changing layer due to the etching effect of the plasma. In the present invention, it is particularly preferable to form the color-changing layer and the non-color-changing layer in such a manner that the color difference between the color-changing layer and the non-color-changing layer can be recognized only after the color of the color-changing layer changes.

To enable the color difference to be recognized, for example, the color-changing layer and the non-color-changing layer may be formed in such a manner that at least one of characters, patterns, and symbols appear only after the color of the color-changing layer changes. In the present invention, characters, patterns, and symbols include any information that notifies color change. Such characters and the like may be suitably designed according to the intended use, etc.

The color of the color-changing layer and the color of the non-color-changing layer before color change may be different from each other. For example, the color-changing layer and the non-color-changing layer may have substantially the same color, and the color difference (contrast) between the color-changing layer and the non-color-changing layer may be made recognizable only after the color change occurs.

The indicator of the present invention is applicable to any plasma treatment using a gas for generating plasma. Thus, the indicator can be used for both reduced-pressure plasma treatment and atmospheric-pressure plasma treatment.

Reduced-pressure plasma treatment may be used, for example, in film production, ashing, cleaning, surface modification, etc., of flat panel displays (e.g., liquid crystal displays); film production, ashing, cleaning, surface modification, etc., in the process of producing semiconductors; cleaning, surface modification, etc., of mounting base materials or printed-circuit base materials; sterilization of medical instruments, etc.; cleaning, surface modification, etc., of mounted components; and the like.

Atmospheric-pressure plasma treatment may be used, for example, in cleaning, surface modification, etc., of flat panel displays (e.g., liquid crystal displays); cleaning, surface modification, etc., of mounting base materials or printed-circuit base materials; surface modification of automobiles, aircraft components, etc.; disinfection, sterilization, medical treatment, etc., in the medical field (dentistry or surgery); and the like.

The gas for generating reduced-pressure plasma may be any gas that can generate plasma by applying AC voltage, pulse voltage, high-frequency waves, microwaves, etc., under reduced pressure. Examples of such gases include oxygen, nitrogen, hydrogen, chlorine, hydrogen peroxide, helium, argon, silane, ammonia, sulfur bromide, water vapor, nitrous oxide, tetraethoxysilane, carbon tetrafluoride, trifluoromethane, carbon tetrachloride, silicon tetrachloride, sulfur hexafluoride, titanium tetrachloride, dichlorosilane, trimethylgallium, trimethylindium, trimethylaluminum, and the like. These gases for generating reduced-pressure plasma may be used singly or in a combination of two or more.

The gas for generating atmospheric-pressure plasma may be any gas that can generate plasma by applying AC voltage, pulse voltage, high-frequency waves, microwaves, etc., at atmospheric pressure. Examples of such gases include oxygen, nitrogen, hydrogen, argon, helium, air, and the like.

These gases for generating atmospheric-pressure plasma may be used singly or in a combination of two or more.

When the indicator of the present invention is used, for example, the indicator of the present invention may be placed in a plasma treatment device using a gas for generating plasma (specifically a device for plasma treatment that generates plasma by application of AC voltage, pulse voltage, high-frequency waves, microwaves, etc., in an atmosphere containing a gas for generating plasma to perform plasma treatment) or disposed on or near the item(s) to be treated that are accommodated in the device, and may be exposed to a plasma treatment atmosphere. In this case, a predetermined plasma treatment can be detected from the color change of the indicator placed in the device.

EXAMPLES

The present invention is described below in more detail with reference to Examples and Comparative Examples. However, the present invention is not limited to the embodiments described in the Examples.

Example 1

A white PET film having a thickness of 188 μm ("Crisper K2323" produced by Toyobo Co., Ltd.) was prepared as a base material. A non-color-changing layer having a thickness of 10 μm was formed on the base material using an ink for forming a non-color-changing layer ("Diatone Ecopure SOY HP J" produced by Sakata Inx Corporation).

Next, a PET film having a thickness of 25 μm ("PET25A PL Shin" produced by Lintec Corporation) was dry-laminated on the non-color-changing layer to form a resin-based transparent cover layer.

Subsequently, a color-changing layer having a thickness of 5 μm was formed on the transparent cover layer using an ink A for forming a color-changing layer.

As a result of the above process, an indicator was prepared.

Composition of the Ink a for Forming a Color-Changing Layer

TABLE 1

| | |
|---|---|
| Pigment Green 7 (phthalocyanine colorant) | 8 |
| PA-100 (polyamide produced by T&K) | 7.1 |
| Nitrocellulose RS7 (nitrocellulose produced by SNPE Japan) | 3.6 |
| Butyl Cellosolve | 64.3 |
| Aerosil R-972 (silica produced by Nippon Aerosil Co., Ltd.) | 14 |
| Nikkol CA2580 (quaternary ammonium salt surfactant produced by Nikko Chemicals Co., Ltd.) | 3 |
| Total | 100 |

Example 2

A white PET film having a thickness of 188 μm ('Crisper K2323" produced by Toyobo Co., Ltd.) was prepared as a base material. A PET film having a thickness of 25 μm ("PET25A PL Shin" produced by Lintec Corporation) was dry-laminated on the base material to form a resin-based transparent cover layer.

Next, a color-changing layer having a thickness of 5 μm was formed on the transparent cover layer using an ink B for forming a color-changing layer.

As a result of the above process, an indicator was prepared.

Composition of the Ink B for Forming a Color-Changing Layer

TABLE 2

| | |
|---|---|
| Pigment Yellow 3 (disazo pigment) | 5 |
| Pigment Green 7 (phthalocyanine colorant) | 7 |
| PA-100 (polyamide produced by T&K) | 7.1 |
| Nitrocellulose RS7 (nitrocellulose produced by SNPE Japan) | 3.6 |
| Butyl Cellosolve | 62.3 |
| Aerosil R-972 (silica produced by Nippon Aerosil Co., Ltd.) | 12 |
| Nikkol CA2580 (quaternary ammonium salt surfactant produced by Nikko Chemicals Co., Ltd.) | 3 |
| Total | 100 |

Example 3

An indicator was prepared in the same manner as in Example 1, except that the resin-based transparent cover layer was formed using a polyester resin solution ("Sundhoma" produced by DIC Corporation). More specifically, a transparent cover layer having a thickness of 10 μm was formed by repeating silk screen printing six times using the polyester resin solution.

Example 4

An indicator was prepared in the same manner as in Example 2, except that the resin-based transparent cover layer was formed using a polyester resin solution ("Sundhoma" produced by DIC Corporation). More specifically, a transparent cover layer having a thickness of 10 μm was formed by repeating silk screen printing six times using the polyester resin solution.

Example 5

An indicator was prepared in the same manner as in Example 1, except that the resin-based transparent cover layer was formed using a UV-curable resin solution ("Raycure Ink" produced by Jujo Chemical Co., Ltd.). More specifically, a transparent cover layer having a thickness of 10 μm was formed by repeating, six times, the step of silk screen printing using the UV-curable resin solution and then curing by UV irradiation.

Example 6

An indicator was prepared in the same manner as in Example 2, except that the resin-based transparent cover layer was formed using a UV-curable resin solution ("Raycure Ink" produced by Jujo Chemical Co., Ltd.). More specifically, a transparent cover layer having a thickness of 10 μm was formed by repeating, six times, the step of silk screen printing using the UV-curable resin solution and then curing by UV irradiation.

Example 7

An indicator was prepared in the same manner as in Example 1, except that an inorganic transparent cover layer (glass) was used in place of the resin-based transparent cover layer. More specifically, glass having a thickness of 10

µm ("Cover Glass" produced by Matsuo Glass) was adhered using an adhesive for glass produced by 3M to form a transparent cover layer.

Example 8

An indicator was prepared in the same manner as in Example 2, except that an inorganic transparent cover layer (glass) was used in place of the resin-based transparent cover layer. More specifically, glass having a thickness of 10 µm ("Cover Glass" produced by Matsuo Glass) was adhered using an adhesive for glass produced by 3M to form a transparent cover layer.

Comparative Example 1

An embodiment such as that in Example 1 except that the transparent cover layer was not formed was used as the indicator of Comparative Example 1.

Comparative Example 2

An embodiment such as that in Example 2 except that the transparent cover layer was not formed was used as the indicator of Comparative Example 2.

Test Example 1 (Plasma Treatment)

Each of the indicators prepared in the Examples and Comparative Examples was placed in a high-frequency plasma device ("BP-1" produced by Samco, Inc.), and plasma was generated using "mixed gas of $O_2$ gas and $CF_4$ gas" or "Ar gas." The change of the base material after reduced-pressure plasma treatment was observed with the naked eye.

As a result of the observation, an indicator in which no powdering was observed on the surface of the base material was evaluated as "A," and an indicator in which powdering was observed on the surface of the base material was evaluated as "B." Table 3 shows the results.

Reduced-Pressure Plasma Treatment Conditions when the Mixed Gas was Used
Device: BP-1 parallel plate high-frequency plasma device (produced by Samco, Inc.)
$O_2$ gas: 10 mL/min, $CF_4$ gas: 5 mL/min
Electric power: 75 W, pressure: 100 Pa, distance between electrodes: 50 mm
Treatment time: 10 min
Reduced-Pressure Plasma Treatment Conditions when the Ar Gas was Used
Device: BP-1 parallel plate high-frequency plasma device (produced by Samco, Inc.)
Ar gas: 20 mL/min
Electric power: 75 W, pressure: 20 Pa, distance between electrodes: 50 mm
Treatment time: 30 min

TABLE 3

|  | Ex. 1 | Ex. 2 | Ex. 3 | Ex. 4 | Ex. 5 | Ex. 6 | Ex. 7 | Ex. 8 | Comp. Ex. 1 | Comp. Ex. 2 |
|---|---|---|---|---|---|---|---|---|---|---|
| Mixed gas | A | A | A | A | A | A | A | A | B | B |
| Ar gas | A | A | A | A | A | A | A | A | B | B |

As is apparent from the results shown in Table 3, in the indicator of the present invention, in which a resin-based or inorganic transparent cover layer was formed, no powdering was observed on the surface of the base material after plasma treatment, whereas, in each of the indicators of the Comparative Examples, in which no transparent cover layer was formed, powdering was observed on the surface of the base material after plasma treatment.

Moreover, in the indicator of the present invention, no curling or color change of the base material was observed after plasma treatment, whereas, in each of the indicators of the Comparative Examples, curling and/or color change of the base material was observed after plasma treatment.

Test Example 1 shows results obtained when reduced-pressure plasma treatment was performed; however, similar effects can also be obtained when the type of plasma treatment is changed to atmospheric-pressure plasma treatment.

DESCRIPTION OF REFERENCE NUMERALS

1. Base material
2. Transparent cover layer
3. Color-changing layer
4. Non-color-changing layer

The invention claimed is:

1. A plasma treatment detection indicator comprising a base material and at least a color-changing layer that changes color in a plasma treatment atmosphere, the color-changing layer being disposed above part or all of a surface of the base material,
   (1) the base material being a fibrous base material or a synthetic resin base material comprising a coloring pigment, and
   (2) a resin-based or inorganic transparent cover layer that covers all of the surface of the base material being disposed between the base material and the color-changing layer,
   wherein the resin-based or inorganic transparent cover layer includes at least one member selected from the group consisting of polypropylenes, polyvinyl chlorides, polyesters, polystyrenes, polyethylenes, polyimides, polyamides, polycarbonates, polyacrylonitriles, and glass.

2. The indicator according to claim 1, wherein the transparent cover layer has a thickness of 5 µm or more.

3. The indicator according to claim 1, wherein the color-changing layer comprises a color-changing colorant that exhibits a change in chemical structure in a plasma treatment atmosphere to change color, and a non-color-changing colorant that does not exhibit a change in chemical structure in a plasma treatment atmosphere.

4. The indicator according to claim 1, wherein the indicator comprises a non-color-changing layer between the base material and the transparent cover layer, the non-color-changing layer comprising a non-color-changing colorant that does not exhibit a change in chemical structure in a plasma treatment atmosphere.

5. The indicator according to claim 4, wherein the non-color-changing layer and the color-changing layer are laminated with the transparent cover layer interposed therebetween in such a manner that the color-changing layer is placed above the non-color-changing layer so that their perimeters are aligned.

* * * * *